United States Patent [19]

Haag, III

[11] Patent Number: 5,615,859

[45] Date of Patent: Apr. 1, 1997

[54] STERILIZABLE VALVE ASSEMBLY

[76] Inventor: Earl C. Haag, III, 2933 Herrlyn Ct., Dallastown, Pa. 17313

[21] Appl. No.: 410,493

[22] Filed: Mar. 24, 1995

[51] Int. Cl.$^6$ .................................................. F16K 7/10
[52] U.S. Cl. ............................................ 251/61.1; 220/232
[58] Field of Search ..................... 251/5, 61.1; 220/232, 220/239

[56] References Cited

U.S. PATENT DOCUMENTS

| | | | |
|---|---|---|---|
| 2,173,570 | 9/1939 | Jesnig | 220/232 X |
| 2,421,847 | 6/1947 | Pfleumer | 220/232 |
| 3,285,308 | 11/1966 | Stanbaugh | 220/232 X |
| 4,003,703 | 1/1977 | Montgomery, Jr. et al. | |
| 4,146,570 | 3/1979 | Nagy . | |
| 4,339,111 | 7/1982 | Welch . | |
| 4,665,653 | 5/1987 | Franz et al. | 220/232 X |
| 4,759,909 | 7/1988 | Joslyn . | |
| 4,779,641 | 10/1988 | Charm et al. . | |
| 5,019,345 | 5/1991 | Lorenz . | |
| 5,113,906 | 5/1992 | Högner . | |
| 5,268,144 | 12/1993 | Heilmann et al. . | |
| 5,352,416 | 10/1994 | Wagner . | |

Primary Examiner—John C. Fox
Attorney, Agent, or Firm—Sixbey, Friedman, Leedom & Ferguson, PC; Jeffrey L. Costellia

[57] ABSTRACT

A valve assembly structure and method for sterilizing multiple environments or containers, such as an isolation barrier and a tank. The valve assembly structure comprises a cylindrical housing with an inner chamber having a first and second opening. The valve assembly further comprises an annular deflatable hollow gasket positioned against the inner chamber for engaging a plug sealing member. The cylindrical housing of the spool may also include a plurality of passages to allow various liquids and gases to be circulated and removed from the inner chamber of the valve assembly. A variety of methods may be employed for adequately sterilizing the valve assembly simultaneously with the multiple sterilized environments or containers. These methods include sterilizing the valve assembly separately through the valve passages in the cylindrical housing of the valve, or sterilizing the valve assembly using the same method or process used to sterilize one or more of the attached containers.

2 Claims, 7 Drawing Sheets

STERILIZABLE VALVE ASSEMBLY

TECHNICAL FIELD OF THE INVENTION

The present invention relates to a valve used in a sterile environment and more particularly, to a valve which may be sterilized either separately or simultaneously with an isolation barrier and/or tank.

BACKGROUND OF THE INVENTION

The pharmaceutical industry is constantly utilizing emerging technologies to produce the highest quality drug products obtainable. In order to ensure quality manufacturing of pharmaceutical products there is a necessity to provide an adequate level of sterility in the equipment and chemicals used. The development of isolation barriers, otherwise known as local controlled environments permits the manipulation of chemicals while maintaining a controlled sterile environment. The isolation barriers may be connected to a tank which can be used to store, mix, or process a sterile chemical or a mixture of sterile chemicals. The tank is typically a stainless steel pressure vessel and may be connected to the isolation barrier by a port which extends into the isolation barrier. The port has a cap that seals the tank during a steam sterilization cycle. Once the tank is sterilized, chemicals may be added to the tank through the connecting port via the isolation barrier.

Many problems and concerns have arisen in using the isolation barrier to maintain a sterile environment and assuring the sterility of all components used, particularly in a drug formulation process. To maintain sterility, both the tank and the isolation barrier require periodic sterilization to ensure that newly added chemicals do not become contaminated by residual chemicals or organisms used in a previous process. One method of maintaining sterility is to clean the tank and isolation barrier manually. However, this method of sterilization may not be validated in view of potential human error in ensuring that all areas the tank and isolation barrier are clean in accordance with federal requirements.

Another common sterility problem involves the use of an isolation barrier to add a sterile powder or a sterile liquid to an already sterile formulation. In this instance, the problem arises when a sterile mixture is introduced into the isolation barrier or tank and additional sterile chemicals need to be added. Before adding the additional chemicals, the isolation barrier requires sterilization. This involves sealing the tank with a cap to maintain the integrity of the tank and/or the sterile chemical mixture in the tank while sterilizing the isolation barrier. When using this method of sterilization, however, the sterility of the area directly under the cap cannot be certain. Hence, any newly added chemicals could be contaminated during this process.

Currently, both the tank and isolation barrier require different methods of sterilization, which the inventor has recognized as causing an additional problem with respect to adequate sterilization. The cap must be on the port leading into the isolation barrier during the steaming of the tank because the isolation barrier is not compatible with steam. The cap must also remain on during the sterilization of the isolation barrier because the tank is not compatible with chemicals used to sterilize the isolation barrier. Therefore, the area between the cap and port again remains unsterilized if these methods of sterilization are employed.

A variety of other sterilization methods have been proposed, however, all of these methods fail to provide adequate sterilization to the tank, the isolation barrier and any connecting valve structure. In particular, U.S. Pat. No. 4,146,570 to Nagy provides a sterilization apparatus and process wherein steam is generated within the apparatus for a specified time period and is released through an evacuating valve located at the bottom of the apparatus. Another prior art method of sterilization is disclosed in U.S. Pat. No. 5,268,144 to Heilmann, which discloses the use of a sterilizing medium which flows into a pressure-tight system for inserting medical devices requiring sterilization. U.S. Pat. No. 5,019,345 to Lorenz discloses a sterilization method which uses a valve structure that opens or closes based on the surrounding pressure or temperature to control the admission or drain of gas used during the sterilization process. Finally, U.S. Pat. No. 4,759,909 to Joslyn discloses a sterilization method comprising the steps of conditioning, steam sterilizing and drying goods placed in a sterilizing chamber. Although the above methods provide sterilization for a single sterile environment, none of these methods provides for different sterilization methods for multiple environments, such as a tank, an isolation barrier and a connecting valve structure when complete sterilization of the entire system is assured.

To ensure adequate sterilization of multiple environments, one proposal included the use of a ball valve between the tank and the isolation barrier. The use of a ball valve, however, created an additional problem due to the size of valve. A four inch ball valve, for example, has a body length of eight to twelve inches. This length creates a surface that is difficult to effectively clean and sterilize. The length also increases the distance from the top of the port to the interior of the tank.

U.S. Pat. No. 4,339,111 to Welch discloses a clean-in-place diaphragm valve having a cleaning fluid outlet used for circulating cleaning fluid through a valve chamber without having to remove the valve. This valve structure, however, is not designed to allow for the sterilization of the valve itself and the containers connected thereto. Therefore, there is no known convenient method of automatically sterilizing a tank, an isolation barrier and a connecting valve structure.

Until recently, the FDA required that drug formulations be performed in Class 100 clean rooms due to the inability to provide an adequate sterile environment. Such clean rooms, however, are expensive to maintain and are not particularly necessary in all drug formulation environments. Therefore, there is a need for an apparatus and method that provide adequate sterilization to multiple environments, that conform to government requirements and that provide a practical solution for the pharmaceutical industry.

SUMMARY OF THE INVENTION

In view of the foregoing, a primary object of the present invention is to overcome the above-noted shortcomings associated with the prior art devices by providing a valve assembly for connecting one or more isolated enclosures.

It is another object of the present invention to provide a valve assembly positioned in an isolation barrier which includes a valve structure that permits effective sterilization of the valve, surrounding isolation barrier and an attached vessel or tank.

It is yet another object of the present invention to provide a valve assembly including a hollow gasket within the valve to engage and disengage a plug inserted therein to allow all areas of the valve to be effectively sterilized while maintaining the stability of attached enclosures and/or vessels.

It is yet a further object of the present invention to provide a valve assembly having a series of passages to allow sterilizing fluids and gases to flow through the valve assembly and effectively sterilize the valve assembly.

It is still another object of the present invention to provide a valve assembly which may be chemically sterilized and steam sterilized while connected to one or more sterilized containers.

It is still a further object of the present invention to provide a valve assembly structure which connects to an isolation barrier and a tank and can be sterilized automatically when either the isolation barrier or tank is sterilized without affecting the condition of the other of the isolation barrier and tank.

It is yet another object of the present invention to provide a sterilization cycle including an initial step for sterilizing a valve assembly connecting an isolation barrier and a tank by inserting a plug into the valve assembly, clamping a cap onto the valve assembly, disengaging a gasket surrounding the plug within the valve assembly from the plug and injecting sterilization liquids or gases into the valve assembly via one or more passages.

It is yet a further object of the present invention to provide a sterilization cycle including a step for sterilizing a tank and a valve assembly connecting an isolation barrier to the tank by inserting a plug into the valve assembly, clamping a cap onto the valve assembly, disengaging a gasket surrounding the plug from the plug, steam sterilizing the connected tank and valve assembly by injecting steam into the tank and valve assembly and returning the tank to atmospheric pressure.

It is still another object of the present invention to provide a sterilization cycle including an additional step for sterilizing an isolation barrier connected to a tank by a valve assembly by inserting a plug into the valve assembly, engaging a gasket surrounding the plug to the plug to provide a seal, and sterilizing the connected isolation barrier by circulating a sterilizing agent into the isolation barrier and valve assembly. Utilizing this series of successive methods permits the sterilization of a tank, a valve assembly connected thereto and an isolation barrier housing the valve assembly without destroying the sterility of any of the individual components subsequent to its own sterilization.

These objects are accomplished by the present invention using an apparatus and method for connecting and adequately sterilizing multiple environments or containers. The present invention comprises a valve assembly structure having a cylindrical housing with an inner chamber and a first and second opening. The cylindrical housing of the valve assembly has one or more passages extending outward from the inner chamber to the outside surface of the housing. These passages connect to ports of the valve assembly which allow various liquids and gases to be circulated and removed from the inner chamber of the valve assembly. The valve assembly further comprises an annular hollow gasket positioned against the wall of the inner chamber. The gasket may be inflated or deflated through a port which extends outward from the gasket through the wall of the cylindrical housing. In addition, the inner chamber of the valve assembly is designed to receive a plug which fits within the cylindrical housing. The bottom of the plug is designed to be horizontally aligned with the annular gasket. The gasket may be inflated to engage the plug and seal the plug within the chamber. A cap is provided to seal the first opening of the valve assembly using one or more clamps. The second opening is preferably sealed onto the port of the tank also using one or more clamps.

DETAILED DESCRIPTION OF PREFERRED EMBODIMENTS

The present invention overcomes the deficiencies of the prior art by providing a simple and effective sealing structure between at least two sterile environments which can itself be sterilized. This permits the introduction of material into a sterile vessel without destroying the sterility of the vessel. It also permits the subsequent addition of different materials without requiring a complete sterilization of the entire system. Specifically, the present invention includes a novel valve assembly connected to a vessel, such as a tank, which permits the effective use of an isolation barrier. This has specific application in the drug formulation industry and should eliminate the need for working in Class 100 clean rooms, which is particularly important in view of recent changes in FDA guidelines for drug formulation.

Figure 1:
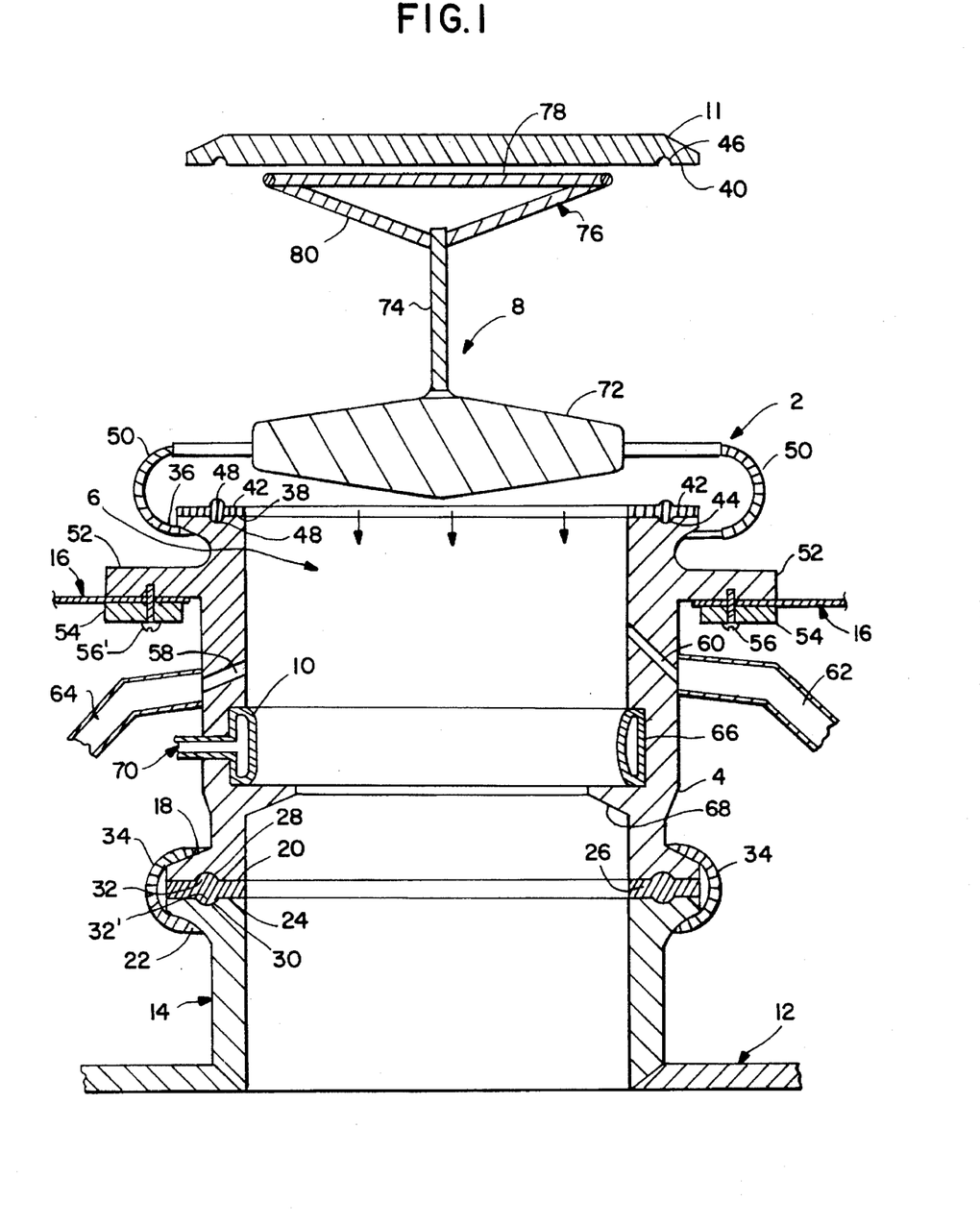
FIG. 1 is a cross-sectional view of an unsealed sterilizable valve assembly in accordance with the first embodiment of the present invention.

Specifically, with reference to the drawings, FIG. 1 illustrates an unsealed sterilizable valve assembly or spool valve 2 in accordance with a first embodiment of the present invention. The spool valve 2 basically comprises a cylindrical housing 4, an inner chamber 6, a plug 8, a hollow gasket 10 which is engagable and disengagable with plug 8 and a cap 11. In the preferred embodiment, spool valve 2 is preferably rigidly connected at one opening or end to a tank 12 via a tank port 14. The opposite end of the spool valve structure is preferably mounted within an isolation barrier 16 which will be discussed in further detail below. The valve assembly of the present invention, however, may be used in any environment which requires a sterilizable valve structure for connecting multiple containers.

The cylindrical housing 4 of the spool valve 2 is a hollow structure manufactured from a rigid, non-corrosive material that is able to withstand high pressures and temperatures, such as aluminum or stainless steel. One skilled in the art will appreciate that any rigid material with the above characteristics may be used. In the preferred embodiment, the housing is between four and eight inches in width, however, the size of the spool valve will vary depending upon the application in which the spool valve is used.

The outer surface of the cylindrical housing 4 is formed with a series of protrusions which extend outwardly from the cylindrical housing body. Specifically, housing 4 has a first protrusion 18 extending outwardly around the periphery of housing 4 adjacent tank port 14 to provide a sealing surface 20. Tank port 14 includes a corresponding protrusion 22 outwardly extending around the periphery thereof to provide a sealing surface 24.

A tank sealing gasket 26 is provided between sealing surfaces 20 and 24 to effectively seal housing 4 to tank port 14. Tank sealing gasket 26 is preferably composed of a rubber or plastic material which can withstand high temperatures and pressures and which is FDA approved as required for the particular use of the spool valve of the present invention. Sealing surfaces 20 and 24 may include annular grooves 28 and 30, respectively, which are preferably formed at the center thereof. These grooves are formed to receive annular projections 32 and 32' of tank sealing gasket 26. Clamp 34 is used to secure first protrusion 18 of housing 4 to protrusion 22 of tank port 14. Clamp 36 may be formed from a metal, such as stainless steel, and must be able to withstand high pressures.

Housing 4 similarly includes a second protrusion 36 to which cap 11 is attached. Specifically, second protrusion 36 includes a sealing surface 38. Cap 11 similarly includes a cap sealing surface 40. A cap sealing gasket 42 is provided between sealing surfaces 38 and 40 to provide an effective seal between housing 4 and cap 11. Sealing surfaces 38 and 40 may also include annular grooves 44 and 46, respectively, which are preferably formed at the center thereof. These grooves are formed to receive annular projections 48 and 48' of cap sealing gasket 42. Clamp 50 is used to secure second protrusion 36 of housing 4 to cap 11. Clamp 50, similar to clamp 34, may be formed from a metal, such as stainless steel, and must be able to withstand high pressures. Cap sealing gasket 40, similar to tank sealing gasket 26, is preferably composed of a rubber or plastic material which can withstand high temperatures and pressures and which is approved by the FDA, as required for the particular use of the spool valve of the present invention.

Cylindrical housing 4 further comprises third annular protrusion 52, which extends along the outer peripheral surface of the cylindrical housing 4 near the second protrusion 36. Third protrusion 52, preferably, secures spool valve 2 to isolation barrier 16, although spool valve 2 may be connected to any number of other types of sterile chambers. FIG. 1 shows third annular protrusion 52 connected to isolation barrier 16 using a mounting ring 54 and screw 56. To mount the spool valve onto the isolation barrier, the valve must be lowered into a hole in the wall of isolation barrier 16 with a diameter larger than the cylindrical housing body 4 but smaller than third annular protrusion 52.

Upon positioning the spool valve 2 within the isolation barrier 16, third annular protrusion 52 is connected to a wall of the isolation barrier 16. Mounting ring 54, preferably composed of metal or other rigid material such as stainless steel, is position against the wall of the isolation barrier 16 opposite third annular protrusion 52. A plurality of screws 56 are threadingly attached through the mounting ring 54 and the wall of the isolation barrier 16. The screws are received by the third annular protrusion 52 and securely tightened to rigidly mount the spool valve 2 to the isolation barrier 16. Of course, numerous other mounting means may be utilized, such as individual mounting nuts, rather than a single mounting ring, as well as adhesives, bolts, etc.

The cylindrical housing 4 of the spool valve 2 further comprises passages, as shown by passages 58 and 60, in FIG. 1. Passages 58 and 60 preferably extend diagonally downward from the wall of the inner chamber 6 in the direction toward the tank to the outer surface of the cylindrical housing 4. Connected to passages 58 and 60 are ports, shown as ports 62 and 64 in FIG. 1. These ports are attached to the outer surface of the cylindrical housing 4 using a welding process or other similar process for securing the ports to the housing 4. Ports 62 and 64 extend from cylindrical housing 4. The length and diameter of these ports may vary depending on the environment in which the spool valve of the present invention is used. These ports are used for inputting and exhausting primarily sterilization materials, such as chemicals or steam. Numerous additional passages and ports may be included to introduce individual materials, and thus, eliminate the need for repeated sterilization of the passages and ports when different materials are required.

Spool valve 2 of the present invention further includes hollow gasket 10, noted above, positioned along the inner wall of inner chamber 6. Hollow gasket 10 is preferably positioned within recess 66 located in inner chamber 6 and abuts an annular ridge 68 extending into inner chamber 6. Hollow gasket 10 may be deflated or inflated using a gasket port 70 which extends outward through the wall of the cylindrical housing 4. An air pump or similar device may be connected to the hollow gasket port 70 to inflate or deflate hollow gasket 10 as necessary. Hollow gasket 10 is preferably composed of a white terpolymer elastomer (EPDM) which is an artificial rubber approved by the FDA for use in sterilized environments. Hollow gasket 10 may be manufactured frown other FDA approved materials for use in sterilized environments or from any material which can be effectively inflated or deflated and can provide a effective seal at high pressures and temperatures.

Plug 8 is used to seal inner chamber 6 of the spool valve 2 from tank port 14. Plug 8 preferably comprises a disc-shaped member 72, a stem 74 attached thereto, and a handle member 76 attached to the stem 74. The handle member 76 preferably includes a circular ring 78 with a plurality of spokes 80 extending diagonally downward from the ring to the stem 74. The spokes 80 are equally spaced and can be spot welded to ring 78 and stem 74. Such a ring and spoke design allows the plug, and particularly the disc-shaped member, to be easily rotated, placed in, or removed frown inner chamber 6 of the spool valve 2. Other handle designs may be equally useful for manipulating disc-shaped member 72 in inner chamber 6.

The disc-shaped member 72 is rigidly attached to stem 74 and tapers outward from its center to the outer perimeter. Handle member 76, stem 74 and disc-shaped member 72 are all preferably manufactured of stainless steel. Nevertheless, one skilled in the art would appreciate that any other material may be used, particularly for disc-shaped member 72, which is FDA approved for its particular use and which is able to withstand high temperatures and pressures.

Figure 2:
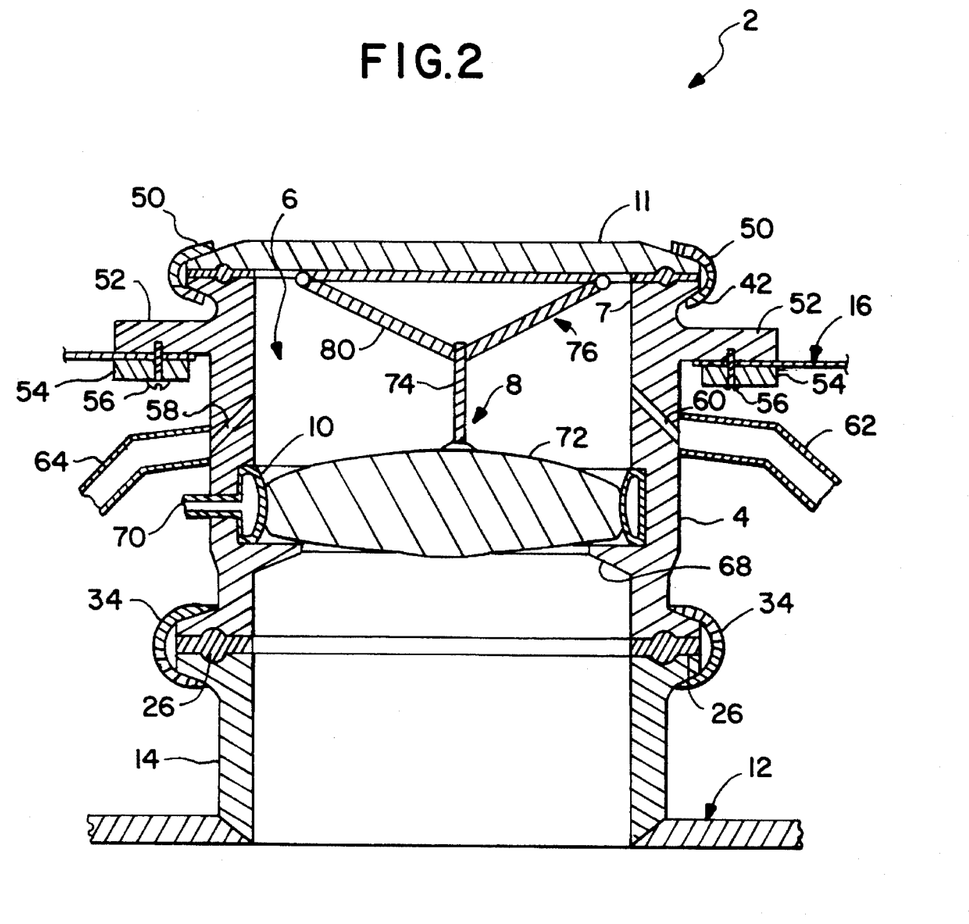
FIG. 2 is a cross-sectional view of a sealed sterilizable valve assembly in accordance with the first embodiment of the present invention.

In the first embodiment, plug 8 is inserted into inner chamber 6 of spool valve 2 and rests on annular ridge 68, as shown in FIG. 2, which illustrates a sealed spool valve. Disc-shaped member 72 sits adjacent hollow gasket 10 and plug 8 is secured within inner chamber 6 by inflating hollow gasket 10 to engage gasket 10 with disc-shaped member 72 to a sufficient degree to create a seal. The process of sealing inner chamber 6 from tank 12 using plug 8 is discussed in further detail below with reference to FIGS. 3a, 3b and 7.

Cap 11 seals the end of the cylindrical housing 4 opposite tank 12, as shown in FIG. 2, which is preferably round in shape with a top surface and a bottom surface. The perimeter of the top surface of the cap 11 may be tapered. Cap sealing gasket 42 is interposed between the cap 11 and cap sealing surface 40 to effectuate a seal. Cap 11 is secured to cylindrical housing 4, as shown in FIG. 2, by clamp 50, which may be formed from any rigid material, such as stainless steel or a plastic material.

The isolation barrier 16 in which spool valve 2 projects is a sterilized environment used for a variety of applications such as mixing chemicals, sterilizing tools, or adding materials to a sterile formulation. The isolation barrier is chemically sterilized and is preferably manufactured from a glass or plastic material, however, any rigid material suitable for use in a sterile environment may be used. A door or other closable opening is generally provided for the isolation barrier to allow for the introduction or removal of materials.

Tank 12 is typically a stainless steel pressure vessel that is preferably sterilized by steam, although other methods of sterilization may be used depending upon the desired use of the tank. Chemicals and other materials are placed into the tank through the isolation barrier and spool valve. The tank may be sterilized while empty using pressurized steam or ingredients mixed in tank 12 may be bulk sterilized using a suitable boiling process.

Both the isolation barrier and the tank are used for drug formulations in the preferred embodiment. These drug formulations must be performed under sterile conditions. For example, the drug formulation ingredients may be sterilized and then mixed in a sterile tank. Alternatively, the ingredients may be mixed and then bulk sterilized using a boiling process, as discussed above. Only about 20 percent of drug formulation processes, however, can survive bulk sterilization because the remaining formulations involve bacteria which may be destroyed by heat, or because the formulations are highly chemical dependent and will, thus, change by heating. Moreover, when using bulk sterilization, the pH value of chemicals may change which will require adjustment by adding an acidic or basic solution. The use of an isolation barrier enclosure permits the introduction of sterile solutions or components to a tank that may or may not contain sterile material without further contamination. The use of an isolation barrier also allows samples to be taken from the tank without fear of contaminating the entire batch. Spool valve 2 of the present invention provides an effective linkage between the isolation barrier and the tank which permits adequate sterilization of the isolation barrier without effecting the tank, as well as permitting sterilization of the entire valve structure itself.

Figure 3A:
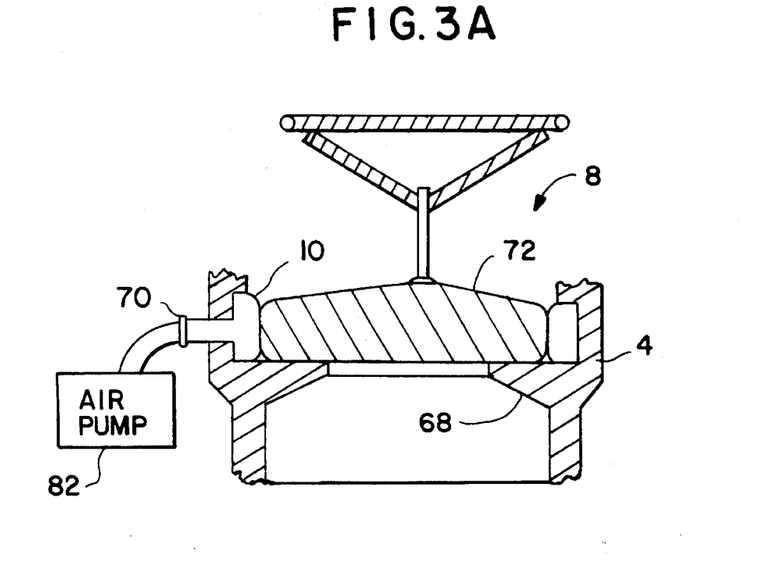
FIG. 3a is a cross-sectional view of an inflated gasket engaging a plug member in a sealed or unsealed sterilizable valve assembly of the present invention.
Figure 3B:
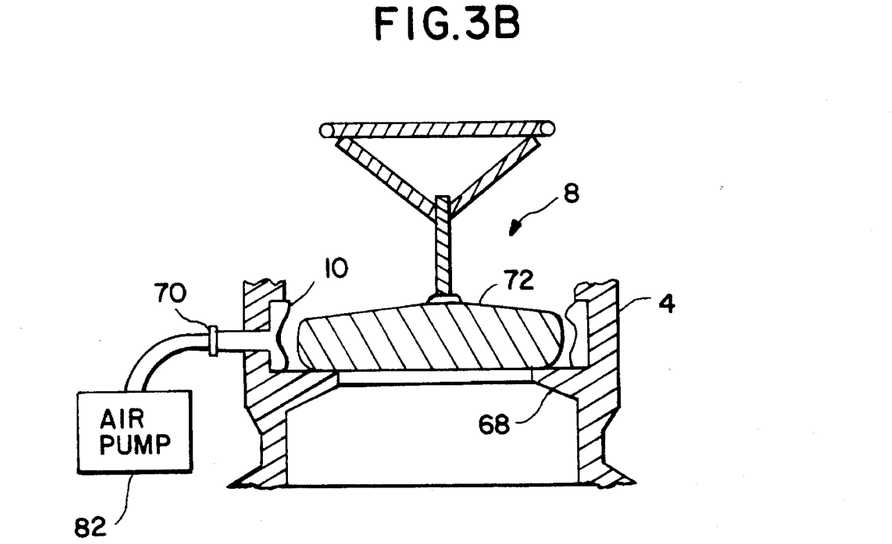
FIG. 3b is a cross-sectional view of a deflated gasket in a sealed or unsealed sterilizable valve assembly of the present invention.

FIGS. 3a and 3b illustrate plug 8 sealed and unsealed, respectively, within inner chamber 6 of spool valve 2 using hollow gasket 10. In particular, FIG. 3a shows disc-shaped member 72 of plug 8 resting on annular ridge 68 within inner chamber 6. An air pump 82 is connected to port 70 to inflate hollow gasket 10 and provide a seal around disc-shaped member 72. Hollow gasket 10 may also be inflated by steam pressure from a steam line. The seal provided by inflated hollow gasket 10 prevents chemicals and/or contaminants from entering the tank 12 through spool wave 2. This is critical to preserving the sterility of the tank environment and, thus, preventing destruction of an entire batch. By sealing plug 8 within the inner chamber 5 as shown in the FIG. 3a, spool valve 2 and isolation barrier 16 can be sterilized without contaminating tank 12.

FIG. 3b shows hollow gasket 10 in a deflated state. In this figure, the air pump is reversed to draw a vacuum to remove air from hollow gasket 10 through port 70. When hollow gasket 10 is in a deflated state, a clearance of about ⅛" is preferred between disc-shaped member 72 and the gasket. This gap ensures that the areas between disc-shaped member 72 and gasket 10 can be sterilized. Hollow gasket 10 may also be used without any external pump connected to port 70 when sterilizing tank 12. In certain processes, the pressure from steam injected into tank 12 during sterilization may be sufficient to deflate hollow gasket 10 and allow steam to penetrate the area between disc-shaped plug member 72 and gasket 10.

Figure 4:
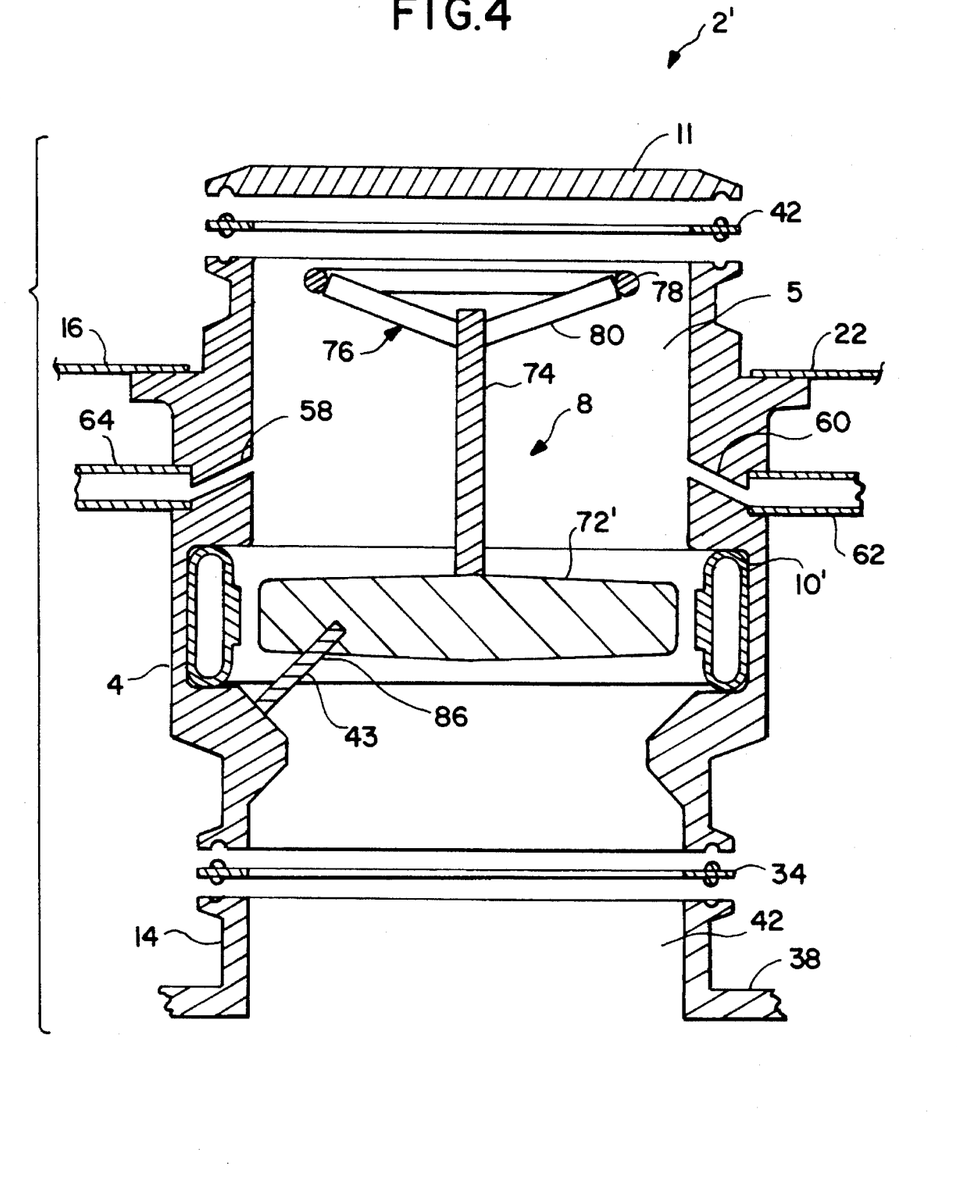
FIG. 4 is a cross-sectional view of a sterilizable valve assembly in accordance with a second embodiment of the present invention.

FIG. 4 illustrates sterilizable spool valve 2' in accordance with a second embodiment of the present invention. In this embodiment, hollow gasket 10' does not engage disc-shaped member 72' unless inflated. Consequently, a space exists between hollow gasket 10' and disc-shaped member 72' when the gasket is at rest without the deflation required in the first embodiment. This space is preferably ⅛" wide. Such distance permits steam to enter the area between the disc-shaped member 72' and the gasket to provide sterilization thereof during the sterilization cycle.

This embodiment also includes a support pin 43 which is rigidly attached to the wall of the inner chamber 5 for securing disc-shaped member 72' in place when inserted into the cylindrical housing 4. The disc-shaped member 72' preferably comprises a series of three equidistant holes 86 on its bottom surface. These holes are formed to receive support pin 43 extending diagonally upward from the inner chamber 6 wall, as shown in FIG. 4. The support pin 43 alleviates the need for an annular ridge 68 to support plug 8. When the plug is secured on the support pin 43, the disc-shaped member 72' is horizontally aligned with hollow gasket 10'. The hollow gasket 10' may then be inflated against disc-shaped member 72' within inner chamber 6.

The spool valve of the present invention permits the cyclic sterilization of a multi-component system which will satisfy FDA standards for sterility in the drug formulation industry and avoid the need for operating in a Class 100 clean room and instead operate in a Class 10,000 or 100,000 clean room. Such a change will greatly reduce the expense of formulating drugs. Specifically, the spool valve of the present invention permits the complete sterilization of a tank to which it is attached, an isolation barrier or related area, also attached to the spool valve, and the spool valve itself without disturbing the sterility of any of the components previously sterilized. The method steps disclosed below will more clearly show the advantageous results obtainable with the spool valve of the present invention. The method steps illustrated in FIGS. 5–7 can be performed as a complete operating cycle for sterilizing a system for initial use or can be used separately to sterilize each component of the system to prevent contamination of the remaining components.

Figure 5:
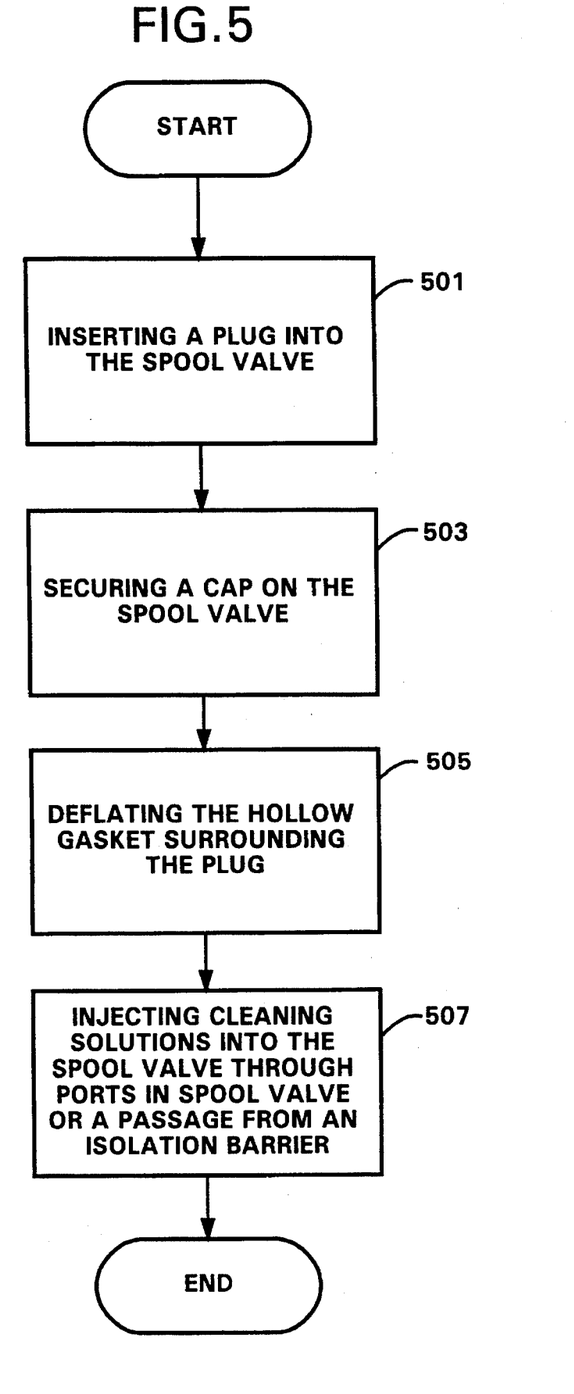
FIG. 5 is a flowchart describing a method of sterilizing the valve assembly of the present invention.

FIG. 5 is a flowchart describing a method of sterilizing the spool valve in accordance with the preferred embodiment of the present invention, as illustrated in FIGS. 1 and 2. Specifically, FIG. 5 describes a method of cleaning the spool valve using passages 58 and 60 or any additional passage in communication with the inner chamber 6 of the spool valve 2. The process begins with step 501 in which plug 8 is inserted into inner chamber 6 of the spool valve 2 as shown in FIG. 1. The plug is pushed into inner chamber 6 until it rests on annular ridge 68, as shown in FIG. 2. In step 503, cap 11 is then secured onto cylindrical housing 4 using clamps 50. In step 505, hollow gasket 10 surrounding disc-shaped member 72 of plug 8 is deflated to provide a gap of at least ⅛" between the disc-shaped member 72 and hollow gasket 10 by pulling a vacuum on the gasket.

Spool valve 2 is then cleaned in step 507 by injecting cleaning solutions into the spool valve 2 through ports 62 and 64 and connected passages 58 and 60 leading into inner chamber 6. Cleaning solutions may include a variety of different materials depending on the type of residue being removed. For example, burned residues are generally removed by an acid or a base, such as phosphoric acid or sodium hydroxide. Further, cleaning solutions may include water or a wide range of detergents. The cleaning solutions may be effectively removed from the spool valve after cleaning by purging the system with steam or water through passages 58 and 60.

Figure 6:
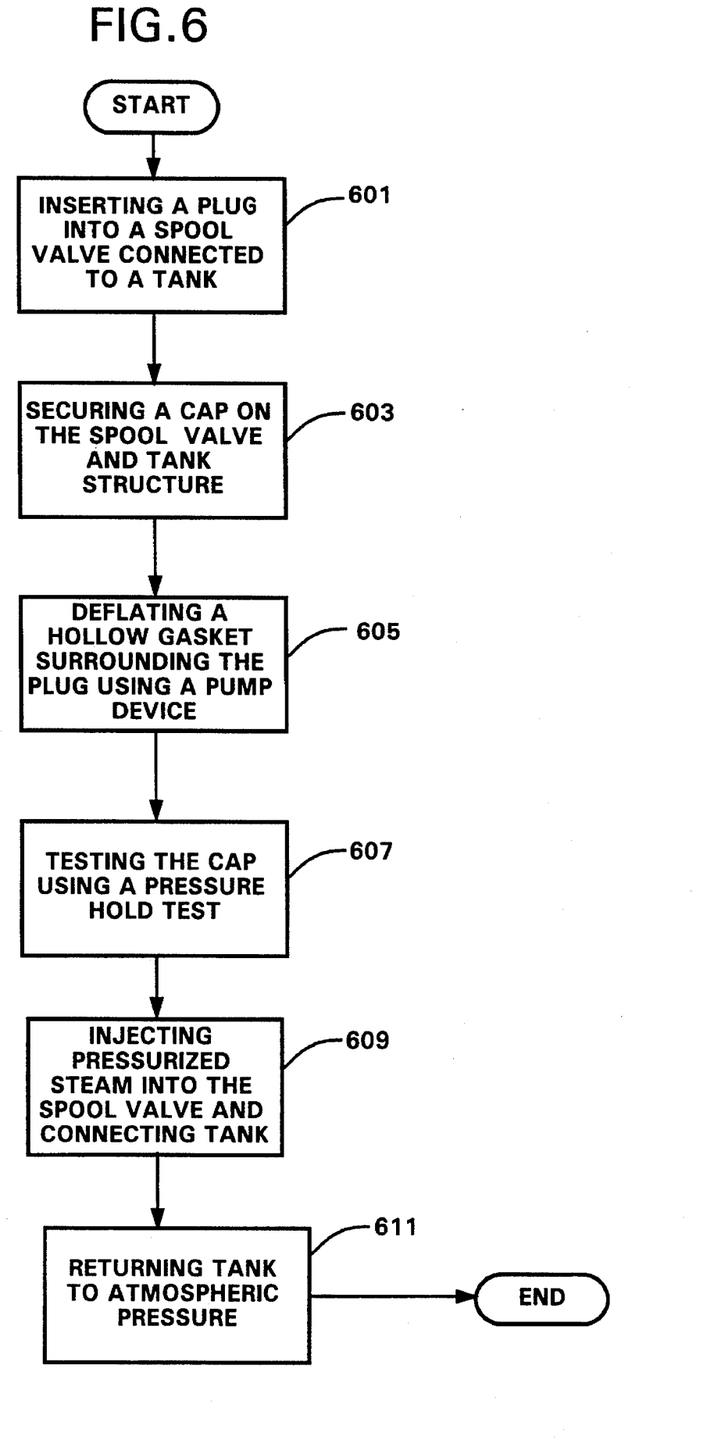
FIG. 6 is a flowchart describing a method of sterilizing the valve assembly and a tank in accordance with the preferred embodiment of the present invention.

Following the cleaning of the spool valve itself, the tank and spool valve may be sterilized by steam. Specifically, FIG. 6 is a flowchart describing the method of sterilizing the spool valve and the tank in accordance with the preferred embodiment of the invention. This portion of the cycle is similar to the process described above with reference to FIG. 5. The process begins with step 601 in which plug 8 is inserted into spool valve 2, as described above, until it rests on annular ridge 68. In step 603, the cap is then secured onto the cylindrical housing 4 using clamp 50. In step 605, hollow gasket 10 surrounding disc-shaped member 72 of plug 8 is deflated to provide a gap of at least ⅛" between the disc-shaped member and the gasket. However, if this is the second step of the cycle following the process described above with reference to FIG. 5, steps 601 to 605 are not required.

A pressure hold test is used in step 607 to determine whether cap 11 is properly secured. The pressure hold test comprises the steps of injecting a predetermined pressure into the inner chamber of the spool valve through tank port 14. This pressure is preferably injected at a pressure sufficient to ensure a proper seal is provided between housing 4 and cap 11. Once cap 11 passes the pressure hold test, pressurized steam is injected into the tank and the connecting spool valve 2, as shown in step 609. The steam is injected into tank 12 itself, as well as into spool valve 2. The steam may enter spool valve through passages 58 and 60 or any additional passage provided into spool valve 2. As noted above, providing additional passages alleviates the need for repeated cleaning and/or sterilization of only a few passages used to input different components. The steam is injected at approximately 35 psig (±5). After the steam sterilizing process, the tank is allowed to cool for approximately 30 minutes and returned to atmospheric pressure, as shown in step 611. Any excess steam may be released from the spool valve through passages 58 and 60.

Figure 7:
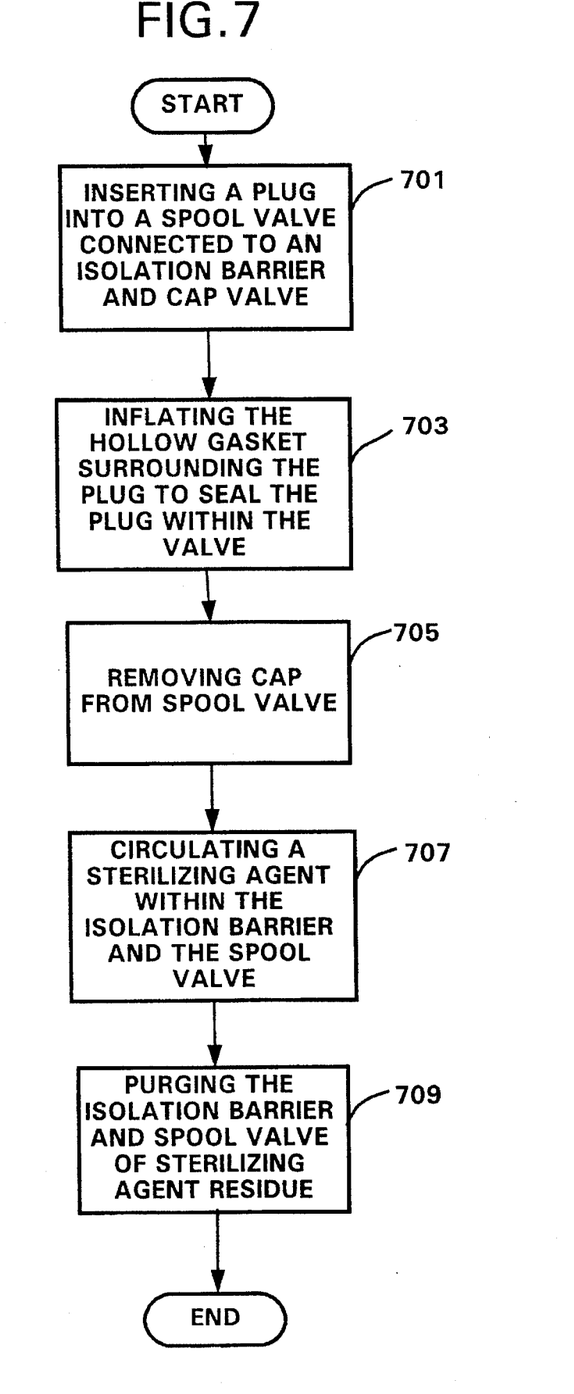
FIG. 7 is a flowchart describing a method of sterilizing the valve assembly and an isolation barrier in accordance with the preferred embodiment of the present invention.

FIG. 7 is a flowchart describing a method of sterilizing the spool valve 2 and the isolation barrier 16 in accordance with the preferred embodiment of the invention. Specifically, FIG. 7 describes a method of sterilizing the spool valve 2 and the isolation barrier 22 at the same time without disturbing the sterility of the tank attached at the opposite end of spool valve 2. The process begins with step 701 in which plug 9 is inserted into a spool valve 2 as shown in FIG. 2. The plug is pushed into inner chamber 6 until it rests on annular ridge 68. As noted above, if the method illustrated in FIG. 7 is part of complete cycle operation following the method of FIG. 6, step 701 is not necessary because the plug is already in place.

In step 703, hollow gasket 10 surrounding disc-shaped member 72 of plug 8 is inflated to engage member 72 to effectively seal plug 9 within the inner chamber 6 of the spool valve 2. Cap 11 is then removed in step 705 so that the interior of the spool valve assembly and the isolation barrier are in fluid communication. Because gasket 10 is engaged with plug 8, the environment established in tank 12 is not effected by this particular process.

The sterilizing process of FIG. 7 begins in step 707 in which a sterilizing agent is circulated within isolation barrier 16 and spool valve 2. The isolation barrier and spool valve is generally cleaned using vaporized hydrogen peroxide to remove impurities. Vaporized hydrogen peroxide cleaning is a proprietary process of AMSCO, Inc. Specifically, hydrogen peroxide is placed on a hot plate of metal, vaporized and carried into the isolation barrier and into the spool valve through passages 58 and 60 or similar passages. A cart is used to provide the vapor and the vapor runs from the cart to the isolation barrier enclosure and spool valve. The isolation barrier enclosure is generally exposed to the vapor for 30 minutes to one hour. After the spool valve 2 and the isolation barrier 22 are sterilized, each area is purged, as shown in step 709, with air or nitrogen until the amount of hydrogen peroxide falls below a predetermined level.

Of course, the methods described above are equally applicable to the second embodiment of the present invention, illustrated in FIG. 4. Specifically, the processing steps discussed above would be the same, except in the methods of FIGS. 5 and 6, hollow gasket 10 does not need to be acted upon because a clearance between disc-shaped member 72' and hollow gasket 10' already exists. The processing steps of the method illustrated in FIG. 7 would be identical.

In addition, in a complete sterilization cycle, the methods illustrated in FIGS. 6 and 7 may be reversed so that the isolation barrier and spool valve are sterilized with chemicals, followed by the steam sterilization of the tank and spool valve. This will permit the complete evacuation of any chemical cleaning residue from the spool valve.

Upon sterilizing spool valve 2, tank 12, and isolation barrier 16, as described in FIGS. 5, 6 and 7, respectively, drug formulation may be performed. Of course, before the drug formulation procedure, the hollow gasket 10 must be deflated and the plug 8 removed. The above procedures are generally performed after each drug formulation step or when otherwise deemed necessary.

While the present invention has been described with reference to a first and second embodiment, it should be appreciated by those skilled in the art that the invention may be practiced otherwise than as specifically described herein without departing from the spirit and scope of the invention. It is therefore, understood that the spirit and scope of the invention be limited only by the appended claims.

INDUSTRIAL APPLICABILITY

The sterilizable spool valve of the present invention may be employed in any environment where it is essential for the complete sterilization of components used in a particular process or environment. This particular sterilizable spool valve is even more appropriate in an environment where a valve connecting one or more containers must itself be sterile to ensure that no contamination results when materials are passed between containers through the valve device.

What is claimed is:

1. A valve assembly for permitting the introduction and removal of material therethrough from at least one enclosure to another comprising:

a cylindrical housing having a first opening and a second opening at each end of said cylindrical housing and an inner chamber therebetween, said inner chamber including an annular ridge adjacent said annular hollow gasket for supporting said annular hollow gasket within said inner chamber of said cylindrical housing, said inner chamber further including a recess portion adjacent said annular ridge for receiving said annular hollow gasket within an inner wall of said inner chamber;

an annular hollow gasket positioned within said inner chamber; and a removable sealing means positionable within said inner chamber for sealing said first opening from said second opening, said annular hollow gasket being engagable with said sealing means by inflation of said annular hollow gasket, said sealing means including a plug member having a first end and a second end, said first end including a handle means for manipulating said plug member within said inner chamber of said cylindrical housing and said second end including a disc-shaped portion positionable within said annular hollow gasket, wherein said cylindrical housing includes a support pin rigidly attached to an inner wall of said inner chamber receivable within a hole provided in a surface of said disc-shaped portion of said plug for securing said plug within said inner chamber.

2. A valve assembly for permitting the introduction and removal of material therethrough from at least one enclosure to another comprising:

a cylindrical housing having a first opening and a second opening at each end of said cylindrical housing and an inner chamber therebetween;

an annular hollow gasket positioned within said inner chamber; and a removable sealing means positionable within said inner chamber for sealing said first opening from said second opening, said annular hollow gasket being engagable with said sealing means by inflation of said annular hollow gasket, wherein said cylindrical housing includes a support pin rigidly attached to an inner wall of said inner chamber receivable within a hole provided in a surface of said sealing means for securing said sealing means within said inner chamber.

* * * * *